United States Patent
Blanz et al.

(10) Patent No.: US 10,061,053 B2
(45) Date of Patent: Aug. 28, 2018

(54) NMR T2 DISTRIBUTION FROM SIMULTANEOUS T1 AND T2 INVERSIONS FOR GEOLOGIC APPLICATIONS

(71) Applicants: Martin Blanz, Celle (DE); Holger Frank Thern, Hannover (DE); Holger Tietjen, Hannover (DE); Mouin Hamdan, Celle (DE); Radu Coman, Hannover (DE)

(72) Inventors: Martin Blanz, Celle (DE); Holger Frank Thern, Hannover (DE); Holger Tietjen, Hannover (DE); Mouin Hamdan, Celle (DE); Radu Coman, Hannover (DE)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 750 days.

(21) Appl. No.: 14/701,008

(22) Filed: Apr. 30, 2015

(65) Prior Publication Data

US 2016/0320519 A1    Nov. 3, 2016

(51) Int. Cl.
*G01V 3/32* (2006.01)
*E21B 47/12* (2012.01)
(Continued)

(52) U.S. Cl.
CPC ............ *G01V 3/32* (2013.01); *E21B 47/12* (2013.01); *G01N 24/081* (2013.01); *G01R 33/448* (2013.01)

(58) Field of Classification Search
CPC ........ G01V 3/32; G01R 33/448; E21B 47/12; G01N 24/081
See application file for complete search history.

(56) References Cited

U.S. PATENT DOCUMENTS 5,486,762 A    1/1996  Freedman et al.
6,005,389 A *  12/1999 Prammer ............. G01N 24/081
                                              324/300
(Continued)

FOREIGN PATENT DOCUMENTS

WO    2009089258 A2    7/2009

OTHER PUBLICATIONS

Notification of Transmittal of the International Search Report and the Written Opinion of the International Searching Authority, or the Declaration; PCT/US2016/029453; dated Aug. 9, 2016; 10 pages.

(Continued)

*Primary Examiner* — Dixomara Vargas
(74) *Attorney, Agent, or Firm* — Cantor Colburn LLP

(57) ABSTRACT

A method for estimating a property of a subsurface material includes conveying a carrier through a borehole penetrating the subsurface material and performing an NMR measurement in a volume of interest in the subsurface material using an NMR tool having an antenna disposed at the carrier. The method further includes receiving with the antenna a short build-up signal due to a short magnetization build-up time of the NMR measurement, an echo-train signal with short polarization time due to the NMR measurement, and an echo-train signal with long polarization time due to the NMR measurement. The method further includes inverting, simultaneously, the short build-up signal, the short-polarization-time echo-train signal, and the long-polarization-time echo-train signal using a processor to estimate the property; and transmitting a signal comprising the property to a signal receiving device.

23 Claims, 7 Drawing Sheets

(51) Int. Cl.
*G01N 24/08* (2006.01)
*G01R 33/44* (2006.01)

(56) References Cited

U.S. PATENT DOCUMENTS

| | | | |
|---|---|---|---|
| 6,049,205 A * | 4/2000 | Taicher | G01N 24/081 |
| | | | 324/303 |
| 6,051,973 A | 4/2000 | Prammer | |
| 6,232,778 B1 | 5/2001 | Speier et al. | |
| 6,255,818 B1 * | 7/2001 | Heaton | G01R 33/563 |
| | | | 324/303 |
| 6,344,744 B2 * | 2/2002 | Taicher | G01N 24/081 |
| | | | 324/300 |
| 6,377,042 B1 | 4/2002 | Menger et al. | |
| 6,452,389 B1 * | 9/2002 | Edwards | G01N 24/081 |
| | | | 324/303 |
| 6,522,137 B1 * | 2/2003 | Sun | G01N 24/081 |
| | | | 324/303 |
| 6,559,639 B2 * | 5/2003 | Minh | G01N 24/081 |
| | | | 324/303 |
| 6,566,874 B1 * | 5/2003 | Speier | G01N 24/081 |
| | | | 324/303 |
| 6,586,931 B2 * | 7/2003 | Taicher | G01N 24/081 |
| | | | 324/303 |
| 6,600,315 B1 | 7/2003 | Heaton et al. | |
| 6,624,629 B1 * | 9/2003 | Speier | G01R 33/4608 |
| | | | 324/303 |
| 6,960,913 B2 | 11/2005 | Heaton | |
| 7,812,602 B2 | 10/2010 | Edwards | |
| 8,395,384 B2 | 3/2013 | Fransson et al. | |
| 9,671,483 B2 * | 6/2017 | Blanz | G01R 33/56509 |
| 2012/0074934 A1 | 3/2012 | Green | |
| 2013/0200890 A1 | 8/2013 | Hursan | |
| 2015/0061664 A1 | 3/2015 | Reiderman et al. | |

OTHER PUBLICATIONS

Coates, et al., "NMR Logging Principles & Applications", Halliburton Energy Survices Publication H02308, 1999, 253 pages.

Dunn, et al; "Nuclear Magnetic Resonance Petropysical and Logging Application"; 2002; Elsevier Science Ltd.; 41 pages.

Fang, Sheng, "Quantification of Hydrocarbon Saturation in Carbonate Formations Using Simultaneous Inversion of Multiple NMR Echo Trains", SPE Annual Technical Conference and Exhibition, Sep. 26-29, 2004, Houston, TX, 12 pages.

Sun, Boqin, "A Global Inversion Method for Multi-Dimensional NMR Logging", Journal of Magnetic Resonance vol. 172, Issue 1, 2005, pp. 152-160.

Xie, Ran-Hong, "A Method for Multiple Echo Trains Jointing Inversion of NMR Relaxation Measurements", Chinese Journal of Geophysics, vol. 52, No. 6, 2009, pp. 1342-1349.

* cited by examiner

US 10,061,053 B2

NMR T2 DISTRIBUTION FROM SIMULTANEOUS T1 AND T2 INVERSIONS FOR GEOLOGIC APPLICATIONS

BACKGROUND

Boreholes are drilled into the earth for many applications such as hydrocarbon production, geothermal production, and carbon dioxide sequestration. In order to efficiently use expensive resources drilling the boreholes, it is important for analysts to acquire detailed information related to the geologic formations being drilled.
Nuclear magnetic resonance (NMR) tools are one type of downhole tools that are particularly useful for performing detailed measurements of properties of hydrocarbon bearing formations. NMR measurements are used to determine among other things, porosity, hydrocarbon saturation, and permeability of rock formations. The NMR logging tools are used to excite the atomic nuclei of the fluids in the geological formations surrounding the borehole so that certain NMR parameters such as hydrogen density, longitudinal relaxation time (generally referred to in the art as $T_1$) and transverse relaxation time (generally referred to in the art as $T_2$) of the geological formations can be measured. From such measurements, the porosity, permeability and hydrocarbon saturation are determined, which provide valuable information about the make-up of the geological formations and the amount of extractable hydrocarbons. The following references may be referred to for teachings with respect to performing NMR measurements: NMR LOGGING PRINCIPLES & APPLICATIONS by George R. Coates, Lizhi Xiao, and Manfred G. Prammer, Halliburton Energy Services Publication H02308 (1999); Nuclear Magnetic Resonance Petrophysical and Logging Applications by K.-J. DUNN, D. J. Bergman and G. A. Latorraca, PERGAMON (2002); and U.S. Pat. No. 6,051,973 to Manfred Prammer.

Unfortunately, tight rock and shale formations produce NMR signals with very short relaxation times $T_1$ and $T_2$. To resolve short $T_2$ components that are less than 0.1 milliseconds in an NMR echo sequence, a very short interecho time (TE) of the order of a few micro-seconds is needed. Normally this is only feasible in laboratory core analyzers that use a relatively high NMR resonance frequency and consequently a relatively high static magnetic field ($B_0$). "Micropores" associated with these kinds of rocks and with some other minerals typically contain water or hydrocarbon (very heavy oil) that, from an NMR perspective (hydrogen), appear almost like a solid component in a $T_2$ distribution. Hydrogen in such "micro-pores" has a very fast decay rate generally due to the micro-pores providing a greater degree of surface area and thus a greater degree of pore wall interface than larger pores. Common NMR logging tools have difficulties and limitations to see this hydrogen signature in these micro-pores while they are readily seen, for example, in the producible water that is associated with larger pores. These difficulties are due to TE times that are relatively large due to the limitation of the technology used.

BRIEF SUMMARY

Disclosed is a method for estimating a property of a subsurface material. The method includes: conveying a carrier through a borehole penetrating the subsurface material; performing an NMR measurement in a volume of interest in the subsurface material using an NMR tool disposed at the carrier, the NMR tool having an antenna; receiving with the antenna a short build-up signal due to a short magnetization build-up time of the NMR measurement; receiving with the antenna an echo-train signal with short polarization time due to the NMR measurement; receiving with the antenna an echo-train signal with long polarization time due to the NMR measurement, inverting, simultaneously, the short build-up signal, the short-polarization-time echo-train signal, and the long-polarization-time echo-train signal using a processor to estimate the property; and transmitting a signal comprising the property to a signal receiving device.

Also disclosed is an apparatus for estimating a property of a subsurface material. The apparatus includes: a carrier configured to be conveyed through a borehole penetrating the subsurface material; a nuclear magnetic resonance (NMR) tool disposed on the carrier and configured to perform an NMR measurement in a volume of interest in the subsurface material, the NMR tool having an antenna configured to at least one of transmit and receive electromagnetic energy; and a processor. The processor is configured to: receive a short build-up signal received by the antenna due to a short magnetization build-up of the NMR measurement; receive a short echo-train signal using the antenna due to the NMR measurement; receive a long echo-train signal using the antenna due to the NMR measurement, the long echo-train having a greater number of echoes than the short echo-train, wherein a magnitude of magnetic polarization of atoms in the volume of interest emitting the long echo-train signal is greater than the magnitude of magnetic polarization of the atoms emitting the short build-up signal and the short echo-train signal; invert, simultaneously, the short build-up signal, the short echo-train signal, and the long echo-train signal using a processor to estimate the property; and transmit a signal comprising the property to a signal receiving device.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the figures.

Disclosed are method and apparatus using nuclear magnetic resonance (NMR) to investigate micro-pores such as those in tight rocks and shale formations. The apparatus and method are based on inverting simultaneously several different phases of NMR measurements in order to determine the full $T_2$ relaxation distribution of a sample, including the micro-porosity range. The method includes simultaneously inverting short $T_1$ build-up signal (e.g., up to TW=10 ms wait time) along with a trainlet (e.g., $T_2$ decay with TW=40 ms wait time) and a long echo-train (e.g., $T_2$ decay fully polarized or more polarized than the build-up and trainlet phases). Because the wait times (TW) can be varied in an NMR tool to provide the three types of signals, very short interecho times (TE), which might be limited by technology, are not required.

Figure 1:
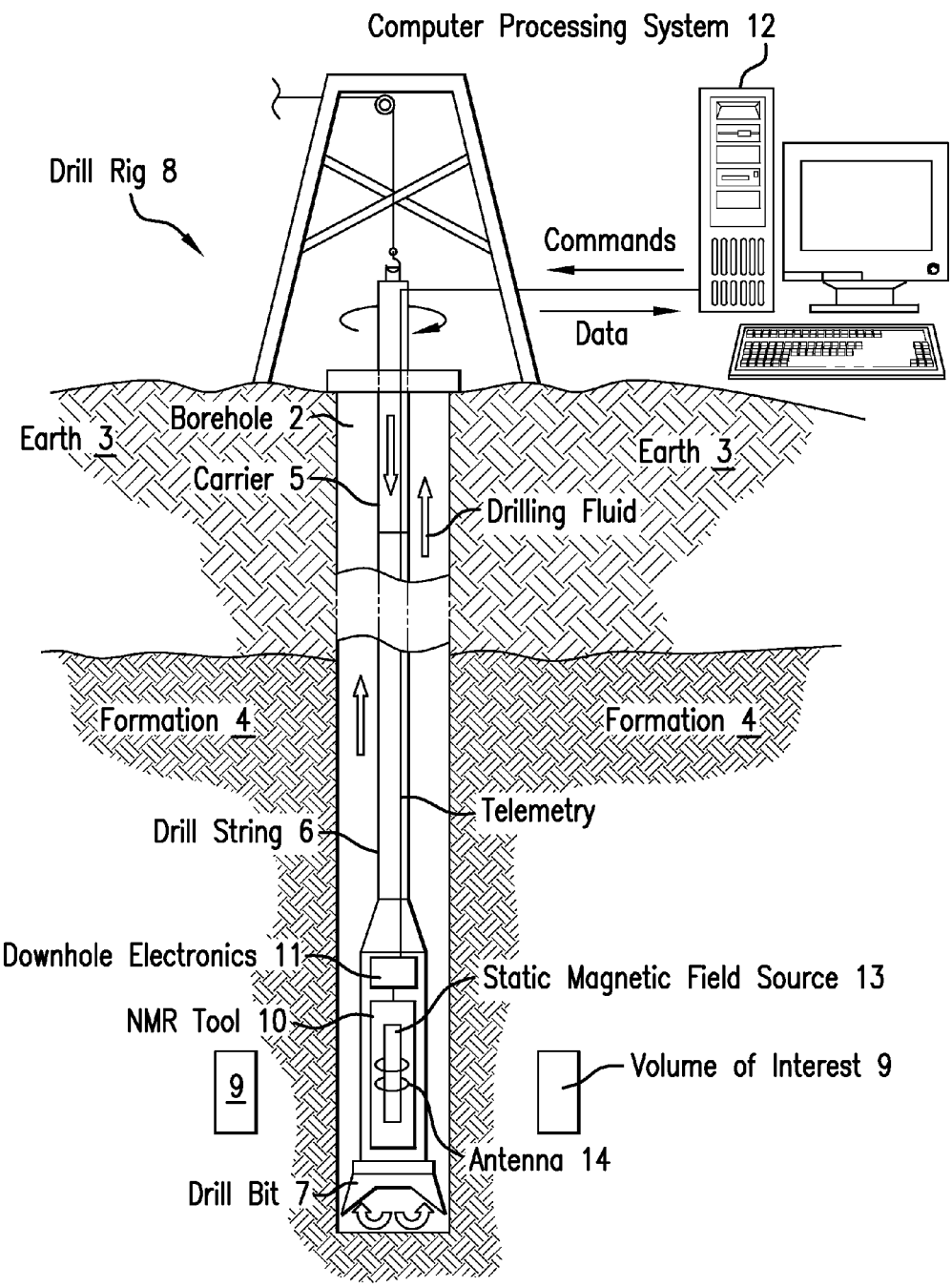
FIG. 1 illustrates a cross-sectional view of an embodiment of a downhole nuclear magnetic resonance (NMR) tool disposed in a borehole penetrating the earth.

FIG. 1 illustrates a cross-sectional view of an embodiment of an NMR tool 10 disposed in a borehole 2 penetrating the earth 3, which includes an earth formation 4. The NMR tool 10 is conveyed through the borehole 2 by a carrier 5, which can be a drill tubular such as a drill string 6. A drill bit 7 is disposed at the distal end of the drill string 6. A drill rig 8 is configured to conduct drilling operations such as rotating the drill string 6 and thus the drill bit 7 in order to drill the borehole 2. In addition, the drill rig 8 is configured to pump drilling mud (i.e., drill fluid) through the drill string 6 in order to lubricate the drill bit 7 and flush cuttings from the borehole 2. Downhole electronics 11 are configured to operate the NMR tool 10, process measurement data obtained downhole, and/or act as an interface with telemetry to communicate data or commands between downhole components and a computer processing system 12 disposed at the surface of the earth 3. Non-limiting embodiments of the telemetry include pulsed-mud and wired drill pipe for real time communications. System operation and data processing operations may be performed by the downhole electronics 11, the computer processing system 12, or a combination thereof. In an alternative embodiment, the carrier 5 may be an armored wireline, which can support and convey the NMR tool 10 and also provide a conductor for communications with the surface processing system 12.

The NMR tool 10 is configured to perform NMR measurements on the formation 4. NMR measurements are performed in a volume of interest 9. This volume may be torus-shaped, surrounding the NMR tool 10, or, when using a side-looking NMR tool, may be on one side only. The NMR measurements may yield a longitudinal relaxation time constant $T_1$ and a transverse relaxation time constant $T_2$ (or distributions thereof, see below). $T_1$ relates to a time that is characteristic of the amount of time required for magnetic polarization of the hydrogen atoms in the volume of interest. In general, longer wait times (TW) provide more magnetic polarization than shorter wait times. $T_2$ relates to an exponential decay time constant that corresponds to a characteristic or property of the formation 4 material. Transverse relaxation relates to the irreversible loss of phase coherence of individual hydrogen nuclei (=protons) in the formation 4 material while precessing about a static magnetic field during an NMR measurement. There is not one single value of $T_2$ for formation rock but a wide distribution of values lying anywhere between fractions of a millisecond (ms) and several seconds for example. The distributions of $T_1$ and $T_2$ values are principal outputs of the NMR tool 10 and together may be referred to as an NMR log. Components in the NMR tool 10 include a static magnetic field source 13 that magnetizes formation materials and an antenna 14, which may represent one or more antennas, which transmit precisely timed bursts of radio-frequency energy (e.g., a CPMG sequence) that provides an oscillating magnetic field. In a time period between these pulses, the antenna receives a decaying echo signal from those protons that are in resonance with the static magnetic field produced by the static magnetic field source. Because a linear relationship exists between the proton resonance frequency and the strength of the static magnetic field, the frequency of transmitted radio-frequency energy can be tuned to investigate volumes of interest having different diameters around the NMR tool 10. It can be appreciated that the NMR tool 10 may include a variety of components and configurations as known in the art of NMR. In that NMR tools are known in the art, specific details of components and configurations of these tools are not discussed in further detail.

It can be appreciated that the NMR tool 10 may be calibrated to a known micro-porosity and/or other known properties of a subsurface material by analysis or by testing in field or laboratory conditions using subsurface materials having a known micro-porosity and/or other known properties.

Figure 2:
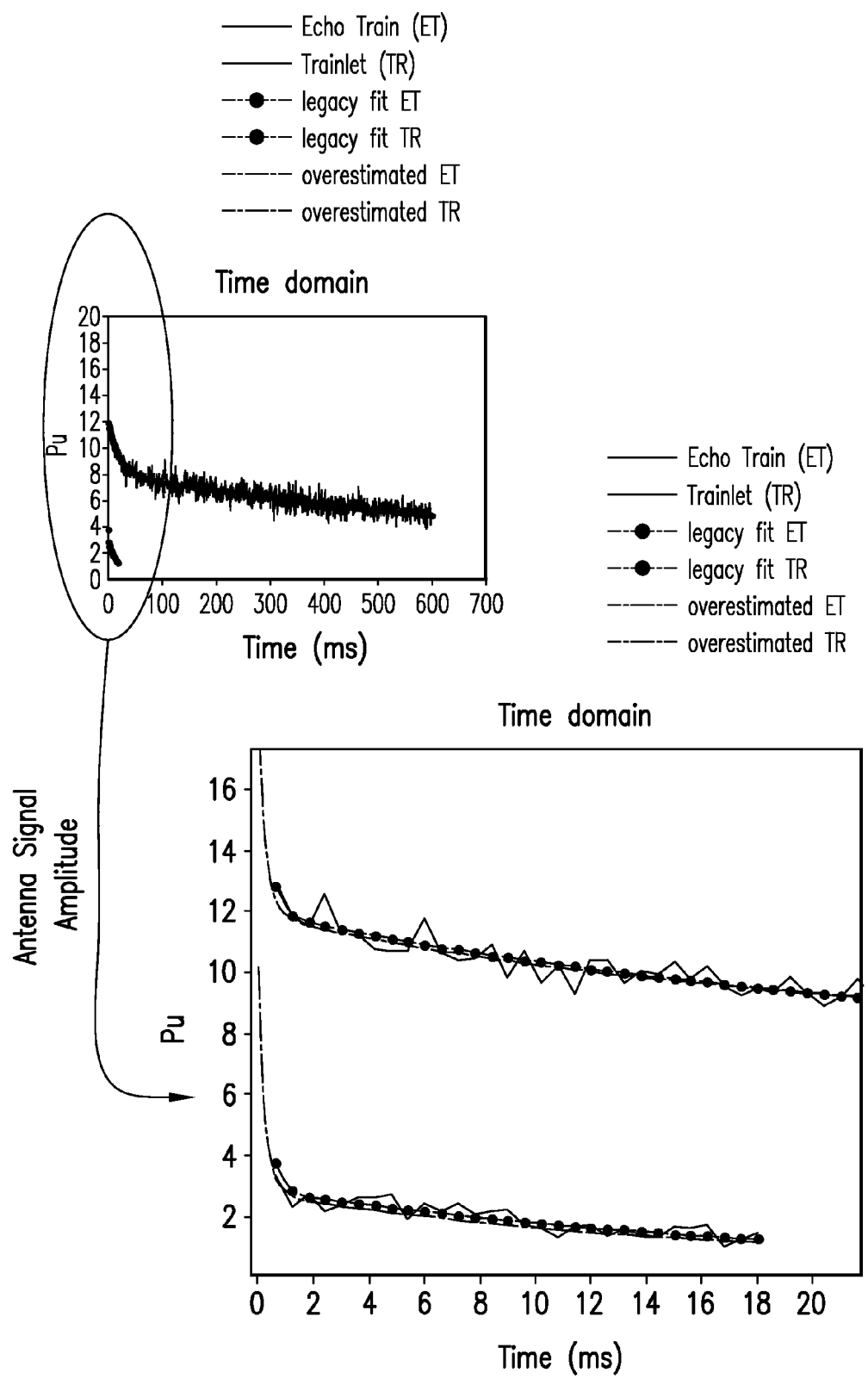
FIG. 2 illustrates one example of one NMR measurement sequence that provides two measurement phases (trainlet and long echo-train) and corresponding signals required for simultaneous inversion.

The NMR tool 10 is configured to provide three phases of NMR measurements—(1) a short build-up phase to provide a short build-up signal received by the antenna 14, (2) a trainlet phase to provide a short echo-train signal received by the antenna 14, and (3) a long echo-train phase that is longer and has more echoes than the trainlet phase to provide a long echo-train signal received by the antenna 14. The references cited in the BACKGROUND may be referred to for information for performing these three phases of NMR measurements. In one or more embodiments, the long echo-train signal is emitted by atoms in the volume of interest having a magnitude of magnetic polarization that is greater than the magnitude of the magnetic polarization of the atoms when they emit the short build-up signal and the short echo-train signal. This can be achieved in one or more embodiments by having a wait time (TW) for producing the long echo-train signal that is longer than the TW for producing the short build-up signal and the short echo-train signal. The measurements related to the three phases may be obtained using one NMR measurement sequence on the volume of interest or may be obtained from two or more NMR measurement sequences on the same or similar volume of interest that are part of other NMR measurements. For example, two or three measurement sequences may be used to provide the three measurement phases. FIG. 2 illustrates one example of one NMR measurement sequence that provides the two measurement phases and corresponding echo train and trainlet required for legacy simultaneous inversion using a T2 span of (0.5 ms to 4096 ms), with the highlight of overestimation in the fit when expanding the T2 span (0.01 ms to 4096 ms).

Figure 3:
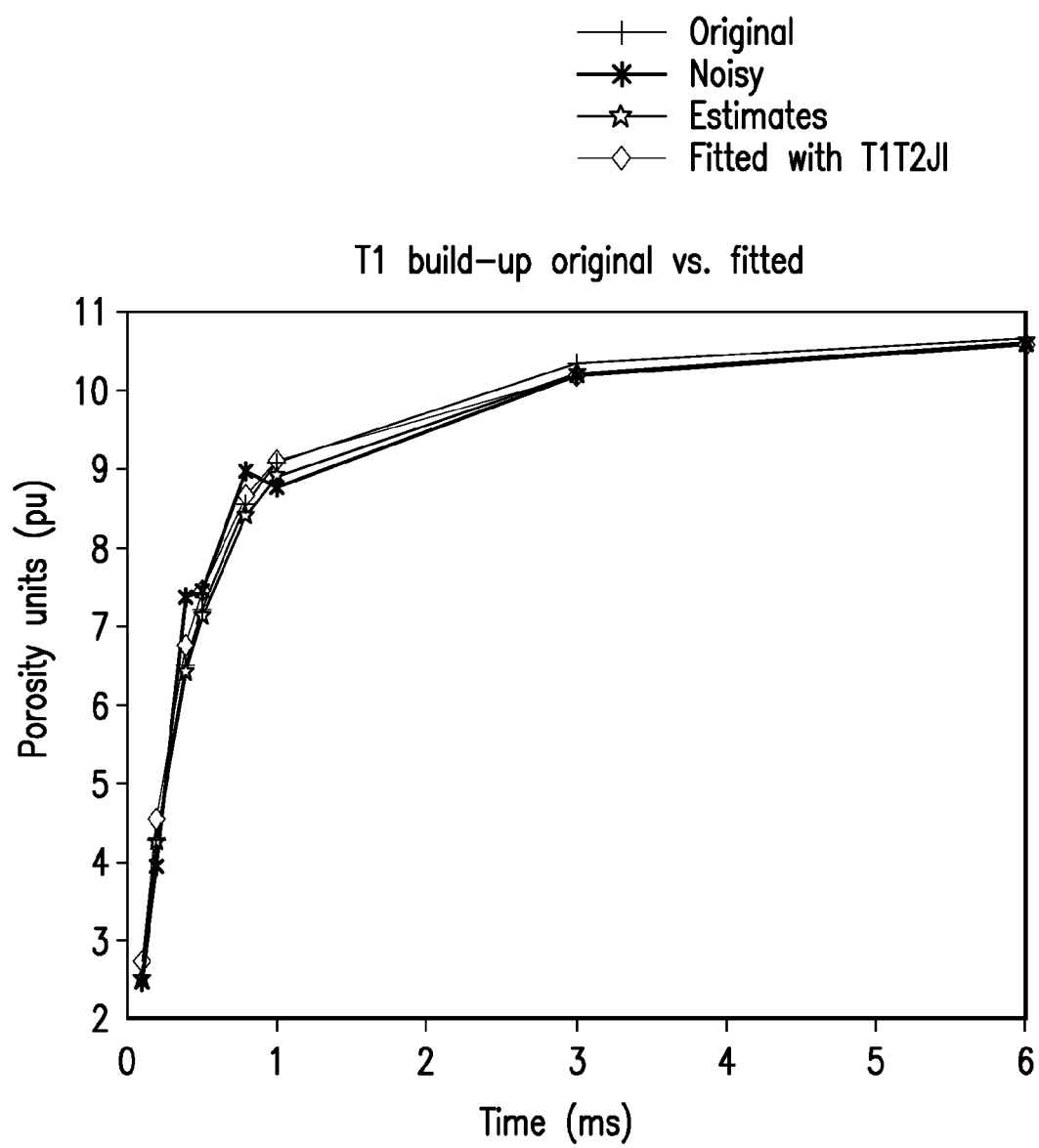
FIG. 3 depicts aspects of an embodiment of a short $T_1$ build-up signal.

FIG. 3 depicts aspects of the short $T_1$ (i.e., magnetic polarization) build-up and the fitted curve from the simultaneous or joint inversion. The NMR signals (i.e., signal amplitude over time) received by an antenna in the NMR tool due to the short $T_1$ build-up may be represented as:

$$\text{Build}(k)_{tws} = \sum_{i:all} \phi_i \cdot (1 - e^{-tws(k)/rT_{2i}})$$

where k is the number of points in the build-up, $T_{2i}$ is the transverse relaxation time constant of the material, $\phi_i$ is porosity for each $T_{2i}$, tws is the short wait time for the magnetization build-up e.g., tws(k)=[0.1, 0.2, 0.4, 0.5, 0.8, 1.0, 3.0, 6.0] ms, and r is $T_1/T_2$ ratio.

Figure 4:
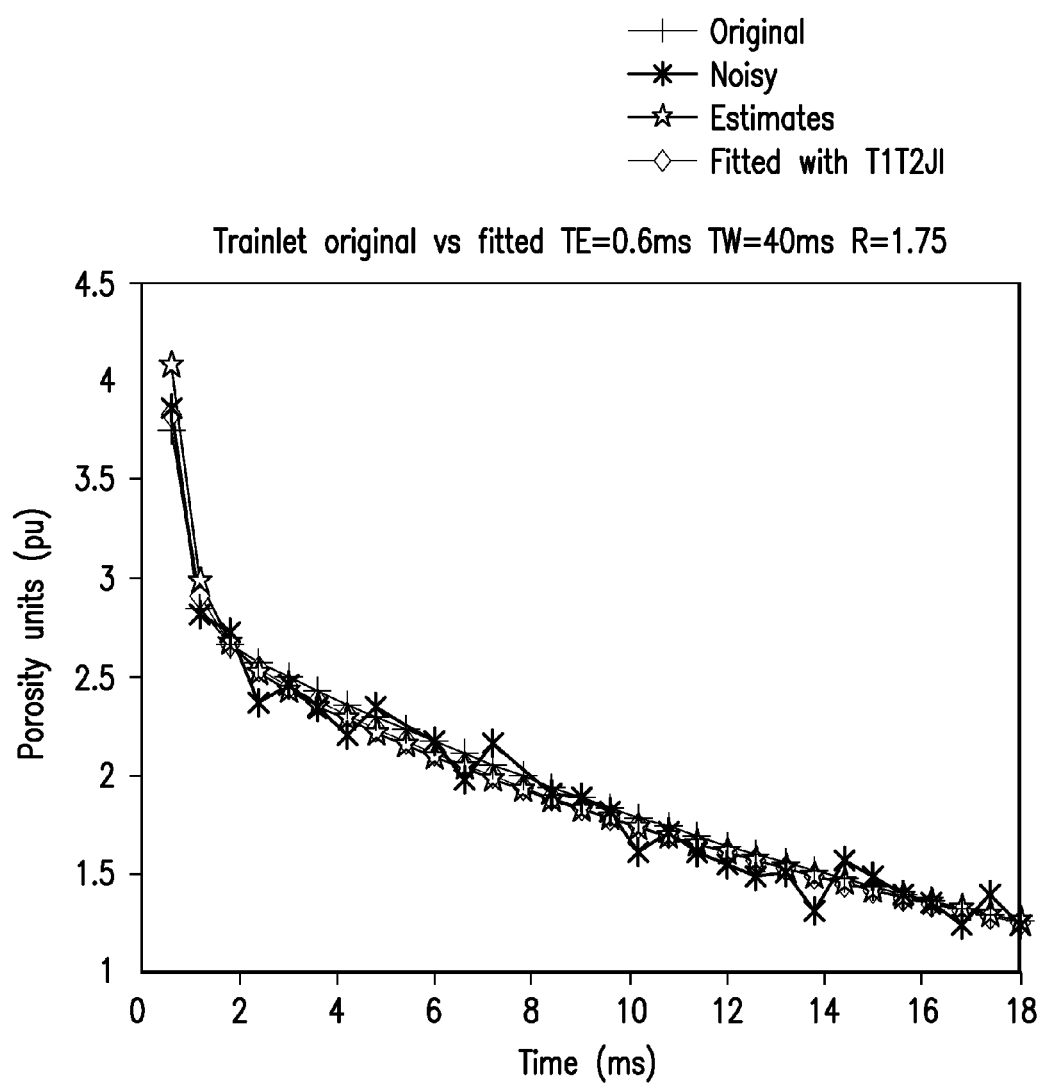
FIG. 4 depicts aspects of an embodiment of a trainlet signal.

FIG. 4 depicts aspects of the trainlet or short echo-train due to the short $T_1$ build-up. The trainlet in FIG. 4 has the inter echo spacing or time (TE) fixed at 0.6 ms, the wait time is 40 ms, and r=(T$_1$/T$_2$) is 1.75. The NMR signals received by an antenna in the NMR tool due to the short echo-train or trainlet may be represented as:

$$ES_{TEs*k} = \sum_{i:all} \phi_i \cdot e^{-TEs*k/T_{2i}} \cdot (1 - e^{-TW/rT_{2i}})$$

where k is the number of echoes, $\phi_1$ is porosity for echo i, TEs is the inter echo time for the short echo-train, T$_{2i}$ is the transverse relaxation time constant for echo i., TW is the wait time, and r is T$_1$/T$_2$ ratio.

Figure 5:
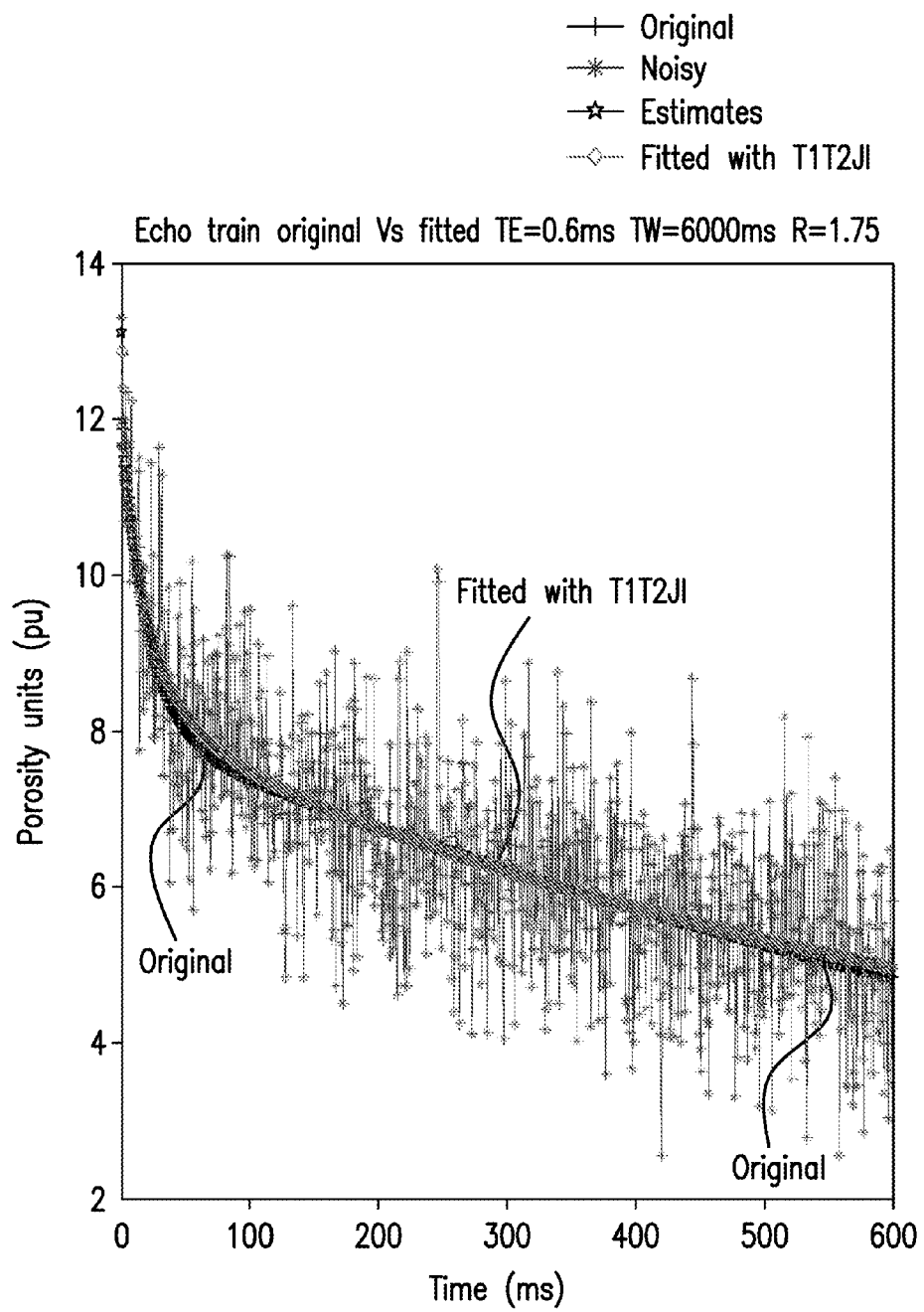
FIG. 5 depicts aspects of an embodiment of a long echo-train signal.

FIG. 5 depicts aspects of the long echo-train resulting from a wait time (TW) of 6000 milliseconds (ms). The longer wait time provides for greater magnetic polarization of atoms in the volume of interest and, thus, a greater number of echoes in the detected echo-train. The long echo-train has the inter echo spacing time (TE) fixed at 0.6 ms and r is 1.75. The NMR signals received by an antenna in the NMR tool due to the long echo-train may be represented as:

$$EL_{TE*k} = \sum_{i:all} \phi_i \cdot e^{-TE*k/T_{2i}}$$

where k is the number of echoes, $\phi_i$ is porosity for echo i, TE is the inter echo time for the long echo-train, and T$_{2i}$ is the transverse relaxation time constant for echo i.

Figure 6:
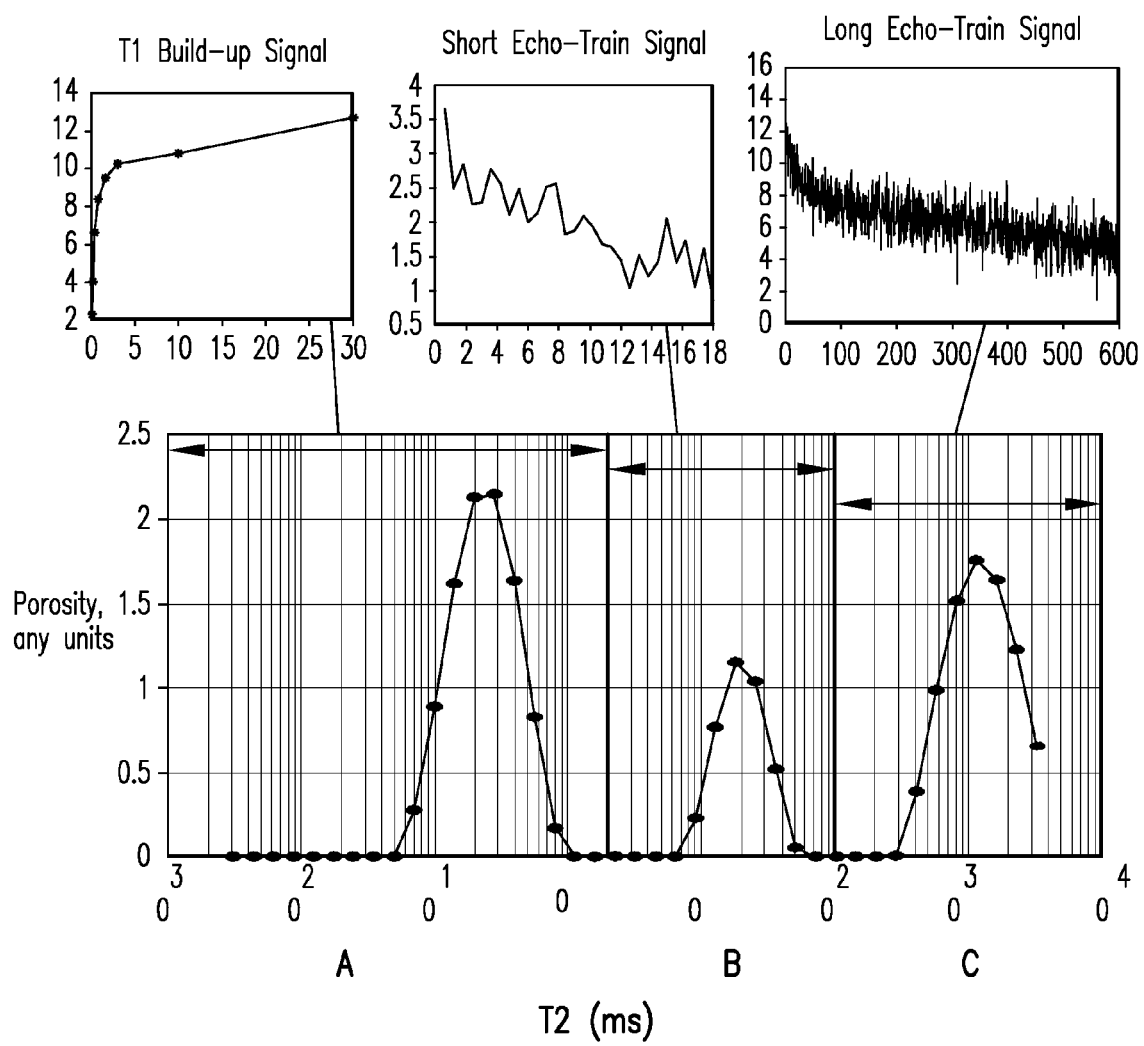
FIG. 6 depicts aspects of splitting the $T_2$ domain into three sections.

FIG. 6 illustrates the resulting porosity as a function of the T$_2$ domain due to the simultaneous inversion to the three NMR measurement phases. Each of the three porosity phases, illustrated as A, B and C, is due mainly or predominantly, but not exclusively, to one on the three NMR measurement phases. While any of the three porosity phases is due to mainly one NMR measurement phase, the other two NMR measurement phases also contribute somewhat due to the simultaneous inversion of all three NMR measurement phases. In this manner, it is possible to measure the porosity of shale and tight rock formations with improved accuracy.

Next, one example of a method for performing the simultaneous inversion to estimate porosity is presented. The example begins with discussing a method of least squares for finding a linear combination of functions that best fits the NMR data of the three NMR measurement phases. It is desired to find a linear combination of functions that best fits a dataset y(x) acquired from an experiment (where y=signal amplitude and x=time) with an estimate ŷ(x). This can be modelled for k different functions in the following general equation.

Given x=[x$_1$x$_2$x$_3$ . . . x$_m$], as a series of indices and $f$(x) as a function of x, then a linear combination of multitude of functions can be represented as:

$$\hat{y}(x) = a_1 f_1(x) + a_2 f_2(x) + \ldots + a_k f_k(x) = \sum_{i=1}^{k} a_i f_i(x).$$

Please note that x could be any series of values and in this application x represents a series of times in milliseconds (not necessarily ordered).

And in vector notation, $$\hat{y} = F \cdot a$$

where a=[a$_1$ a$_2$ a$_3$ . . . a$_k$]$^T$ is a column vector and F=[$f_1$ $f_2$ . . . $f_k$] is a m by k matrix formed of the various different function vectors where $f_k$ is a column vector function evaluated at each x$_m$.

It may be observed that a perfect linear relationship is unlikely. There are different reasons for this. For example, experimental error and/or the underlying relationship may not be exactly linear, but rather only approximately linear. A measure that will indicate the excursion from our fit to the acquired data may be the residual r(x) between the measured data and its estimate.

This is to say: $r(x) = \hat{y}(x) - y(x)$.

And in vector notation, $$r = \hat{y} - y = (F \cdot a) - y.$$

This shows what the error looks like, but it does not show how bad this error is or if there is another manifestation of the error that makes the fit better. From the r(x) equation above, it can be deduced that the best fit is when r(x)=0. This may be virtually impossible in the presence of noise in the acquired data for reasons mentioned earlier. A good attempt is to make this error to be a minimum.

Next, a norm approximation for minimizing r(x) is discussed. The simplest norm approximation is an unconstraint problem of the form:

minimize $\|F \cdot a - y\|$

Minimizing the error between measured y(x) and its estimate ŷ(x), a second order equation may be selected where its minimum would be achieved when its derivative with respect to a is equal to zero.

One norm approximation involves the Euclidean or L2-norm. By squaring the objective, an equivalent problem is obtained, which is called the least-square approximation problem, minimize $\|F \cdot a - y\|_2^2 = r_1^2 + r_2^2 + r_3^2 + r_4^2 + \ldots + r_m^2$ where the objective is the sum squared of the residual. This problem can be solved analytically by expressing the objective as a convex quadratic function.

This is to say: minimize the sum of error squared $([r(x)]^2) \rightarrow (\hat{y}(x) - y(x))^2$.

Putting this equation in vector format to minimize G(a) with respect to a:

$$G(a) = \min_a \|r\|_2^2 = r^T \cdot r = 0 \Rightarrow (F \cdot a - y)^T \cdot (F \cdot a - y)$$
$$= a^T \cdot F^T \cdot F \cdot a - 2 \cdot a^T \cdot F^T \cdot y + y^T \cdot y$$

and the derivative with respect to a is $$\frac{\partial G}{\partial a} = 2 \cdot F^T \cdot F \cdot a - 2 \cdot F^T \cdot y.$$

As $y^T \cdot y = 0$ since it does not depend on a, thus at minimum the derivative is set to zero, $$\frac{\partial G}{\partial a} = 2 \cdot F^T \cdot F \cdot a - 2 \cdot F^T \cdot y = 0 \Rightarrow (F^T \cdot F) \cdot a = F^T \cdot y.$$

This provides a solution for vector a: $a = (F^T \cdot F)^{-1} \cdot F^T \cdot y$ where $(F^T \cdot F)^{-1} \cdot F^T = F^+$ is called a pseudo inverse of F.

Next, a method of weighted linear least squares is discussed. When acquiring the NMR data, each and every data point may be weighted by its variance as it would give different relative emphasis to different components of the residual (error). In one or more embodiments, the signal-to-noise ratio (SNR) for each data point may be used to provide the weight for that data point such that data points having a higher SNR are weighted higher than data points having a lower SNR. As an example of the weighting matrix, let $$W_{m \times m} = \begin{bmatrix} 1/2 & 0 & \cdots & \cdots & 0 \\ 0 & \ddots & 0 & 0 & 0 \\ \vdots & 0 & \ddots & 0 & \vdots \\ \vdots & 0 & 0 & \ddots & \vdots \\ 0 & \cdots & \cdots & \cdots & 1/\sqrt{2} \end{bmatrix}.$$

If the matrices $F^* = W^*F$ and $y^* = W^*y$ are used, then the equation for a above may be written as $$a = (F^{*T} \cdot F^*)^{-1} \cdot F^{*T} \cdot y^*$$

Next, application of a penalty function is discussed. Penalized least squares estimation differs from classical least squares estimation because the solution a is obtained by minimizing an objective function that involves a penalty function on top of the sum of squared residuals. The idea of the penalty function is that it prevents over estimation: a penalty is incurred whenever a factor effect has a nonzero estimate, i.e. whenever a term is included in the model. Therefore, factor effects only get positive estimates if the resulting penalty is compensated by a substantial decrease in the sum of squared residuals. The following section on regularization is a form of penalization.

Next, regularization or smoothing is discussed. The goal of a basic regularization is to find a vector a that makes the residual small. This is described as a vector optimization with two objectives, $\|F \cdot a - y\|$ and $\|a\|$ in a bi-criterion way, by adding an extra term or penalty function associated with the norm a. In other words, minimize $\|F \cdot a - y\|^2 + \lambda \|a\|^2$ for $\lambda > 0$. This is referred to as Tikhonov regularization. In one useful extension, $\|a\|$ can be replaced by $\|D \cdot a\|$ where D is a regularization matrix representing prior knowledge about the result a. One representation of D is a second order differentiation operator so $\|D \cdot a\|$ represents a measure of variation or smoothness of the result a.

$$D = \begin{bmatrix} 1 & -2 & 1 & 0 & 0 & & 0 & 0 & 0 \\ 0 & 1 & -2 & 1 & 0 & \cdots & 0 & 0 & 0 \\ 0 & 0 & 1 & -2 & 1 & & 0 & 0 & 0 \\ & & \vdots & & \ddots & & & \vdots & \\ 0 & 0 & 0 & 0 & 0 & & 1 & 0 & 0 \\ 0 & 0 & 0 & 0 & 0 & \cdots & -2 & 1 & 0 \\ 0 & 0 & 0 & 0 & 0 & & 1 & -2 & 1 \end{bmatrix}$$

Next, a final generalized model is discussed in which error e is represented as $$\|e\|^2 = ((F \cdot a) - y)^T \cdot W \cdot ((F \cdot a) - y) + \lambda \cdot a^T \cdot D \cdot a$$

where W is a data weighting matrix and D is a regularization matrix, also known as smoothing matrix, representing a prior knowledge about the result a, and $\lambda$ is the regularization parameter. The resulting expression for a is:

$$0 = F^T \cdot W \cdot F \cdot a + \lambda \cdot D \cdot a - F^T \cdot W \cdot y$$

This expression can be solved using many different methods from conventional inversion to singular value decomposition. The weighting matrices can be selected to be any that satisfy the problem and taking into account prior knowledge of the problem being solved.

Next, solving simultaneous equations representing the three phases of NMR measurements is discussed. This involves creating:
1—the joint F matrix (i.e., Forward matrix).
2—the weight matrix W.
3—the traces (i.e., echoes) to which y is being fit.
These are augmentation of matrices (appending to matrices other sub matrices while keeping the corresponding equations). The smoothing matrix D is already defined. The matrix a is then solved for with setting $\lambda$ to 0.8.

$$F = \begin{bmatrix} FL_{1000 \times 41} \\ \hline FS_{60 \times 41} \\ \hline FB_{8 \times 41} \end{bmatrix}; W = \begin{bmatrix} W1_{1000 \times 1000} & 0 & 0 \\ 0 & W2_{60 \times 60} & 0 \\ 0 & 0 & W3_{8 \times 8} \end{bmatrix};$$

$$y = \begin{bmatrix} EL_{1000 \times 1} \\ \hline ES_{60 \times 1} \\ \hline EB_{8 \times 1} \end{bmatrix}$$

where:

$$EL_{TE*k} = \sum_{i:all} \phi_i \cdot e^{-TE*k/T_{2i}} \Rightarrow EL_{1000 \times 1} = FL_{1000 \times 41} * a_{41 \times 1} \rightarrow \text{long echo-train}$$

$$ES_{TEs*k} = \sum_{i:all} \phi_i \cdot e^{-TEs*k/T_{2i}} \cdot (1 - e^{-TW/rT_{2i}}) \Rightarrow ES_{30 \times 1} =$$

$$FS_{30 \times 41} * (R_{41 \times 1} \cdot a_{41 \times 1}) \rightarrow \text{trainlet}$$

$$Build_{tws} = \sum_{i:all} \phi_i \cdot (1 - e^{-tws/rT_{2i}}) \Rightarrow EB_{8 \times 1} =$$

$$FB_{8 \times 41} * (R_{41 \times 1} \cdot a_{41 \times 1}) \rightarrow T_1 \text{ build up.}$$

By iterating $r = (T_1/T_2)$ from 1.0 to 6.0, different curve fits will be obtained via a linear least square method. The r resulting in the minimum sum of errors squared will define the best fit, with positivity of the final result taken into account i.e. setting negative results to zero and redo the fit.

Figure 7:
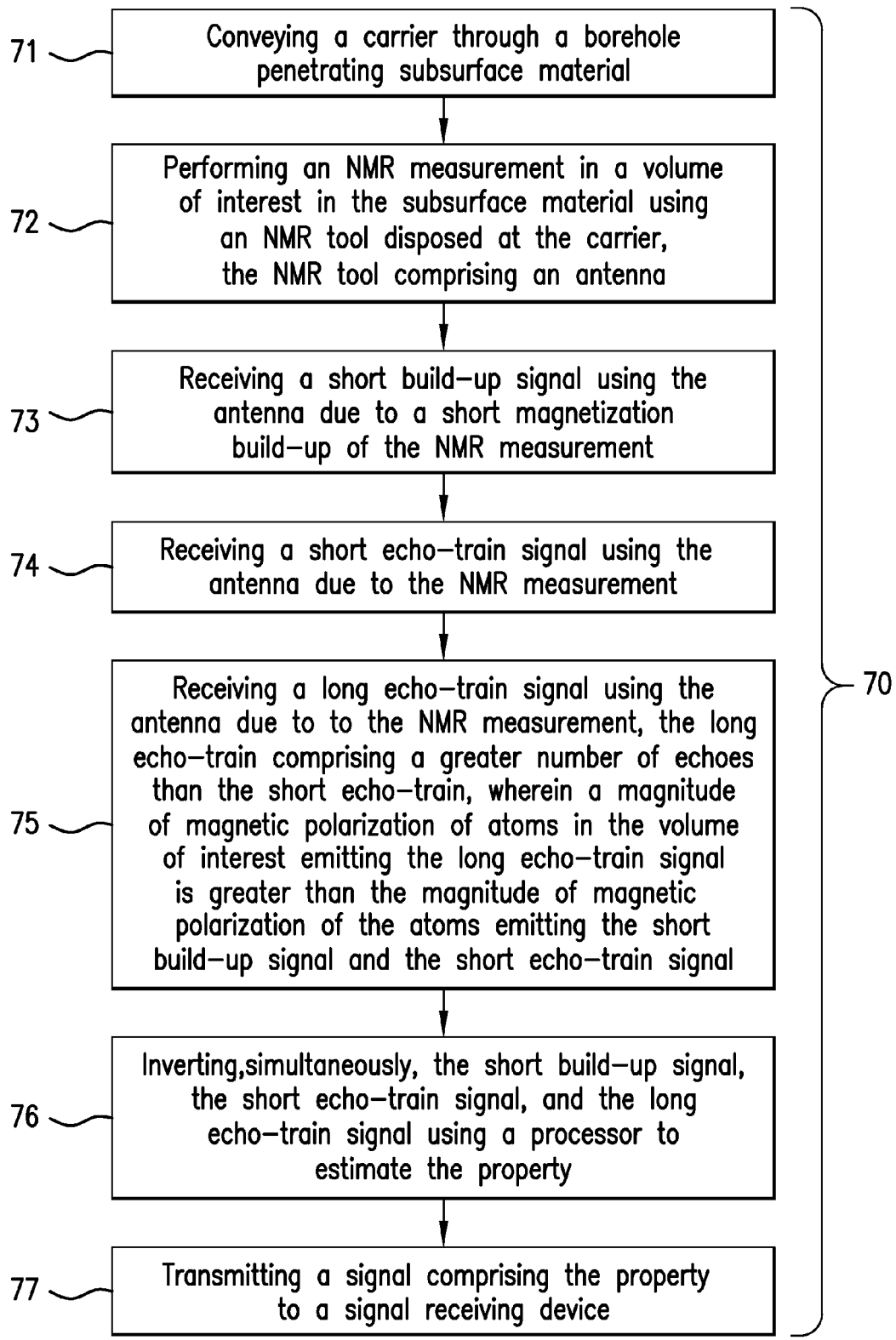
FIG. 7 is a flow chart for a method for estimating a property of an earth formation penetrated by a borehole.

FIG. 7 is a flow chart for a method 70 for estimating a property of a subsurface material. In one or more embodiments, the property is porosity, which may include total porosity or fractional porosity. In one or more embodiments, the subsurface material has micro-pores, such as those in tight rocks and shale formations, which may be characterized by having a $T_2$ time of three (3) milliseconds or less. In one or more embodiments, micro-pores having a T2 time of one (1) millisecond or less may be investigated and a property estimated using the method 70. In one or more embodiments, the subsurface material is characterized by having a $T_2$ time in a range of one hundred microseconds to three (3) milliseconds. Block 71 calls for conveying a carrier through a borehole penetrating the subsurface material. Block 72 calls for performing an NMR measurement using an NMR tool disposed at the carrier, the NMR tool comprising an antenna. Block 73 calls for receiving a short build-up signal using the antenna due to a short magnetization build-up of the NMR measurement. Block 74 calls for receiving a short echo-train signal using the antenna due to the NMR measurement. Block 75 calls for receiving a long echo-train signal using the antenna due to the NMR measurement, the long echo-train having a greater number of echoes than the short echo-train, wherein a magnitude of magnetic polarization of atoms in the volume of interest emitting the long echo-train signal is greater than the magnitude of magnetic polarization of the atoms emitting the short build-up signal and the short echo-train signal. In one or more embodiments, the greater magnitude of magnetic polarization is achieved by applying a longer wait time (TW) using the NMR tool in order to have more time for greater build-up of magnetic polarization in the volume of interest. Block 76 calls for inverting, simultaneously, the short build-up signal, the short echo-train signal, and the long echo-train signal using a processor to estimate the property. In general, inverting the short build-up signal (Build), the short echo-train signal (ES), and the long echo-train signal (EL) simultaneously to estimate the property relates to establishing a curve that provides a best fit simultaneously to the Build, ES and EL signals. Block 77 calls for transmitting a signal comprising the property to a signal receiving device. In one or more embodiments the signal receiving device may be a computer display or printer for presenting the estimated property to a user or a storage medium or memory for storing the estimated property.

In one or more embodiments, simultaneously inverting the Build, ES and EL signals includes: (i) establishing a linear combination of functions that best fits the short build-up signal, (ii) the short echo-train signal, and the long echo-train signal; (iii) establishing a norm approximation that minimizes error e between the linear combination of functions and the short build-up signal, the short echo-train signal, and the long echo-train signal; (iv) weighting data points in each of the short build-up signal, the short echo-train signal, and the long echo-train signal, wherein the weighting may be in accordance with a signal-to-noise (SNR) value associated with each of the data points such that data points associated with higher SNR values are weighted more than data points associated with lower SNR values; (v) applying a penalty function to the norm approximation, wherein the penalty function may include applying regularization to the norm approximation; (vi) establishing a generalized model representing the error e, the generalized model comprising a data weighting matrix W, a regularization matrix D representing a prior knowledge about a result a, a regularization parameter $\lambda$, and a parameter $r=T_1/T_2$; iterating r in the generalized model to determine a resulting r that provides a minimum sum of errors squared to provide a best fit curve; and estimating the parameter using the best fit curve.

The above disclosed method and apparatus provide several advantages especially when compared to prior art NMR tools in that subsurface materials, such as tight rocks and shale formations, having $T_2$ time constants of three milliseconds or less can be accurate characterized to estimate porosity. Accurately capturing fast decaying $T_1$ and $T_2$ signals has a variety of applications such as unconventional reservoirs, microporosity, and clay-bound water. For unconventional reservoirs, it is commonly accepted that due to the small pore sizes and the wettability conditions in unconventional shale reservoirs, the primary NMR signals are expected in the sub-millisecond to tens of milliseconds range. Current NMR interpretation approaches are limited by not accurately capturing fast $T_1$ and $T_2$ signals for differentiating fluid components such as clay-bound water vs. producible hydrocarbon. The method and apparatus disclosed herein is able to differentiate between these fluid components. Regarding microporosity, in conventional carbonate reservoirs important fluid components are associated with fast decaying $T_1$ and $T_2$ components. These fluid components are generally referred to as microporosity. Typically, microporosity is considered to not contribute to the flow properties and the storage of hydrocarbons because they previously could not be accurately characterized. Therefore, the quantification of microporosity in carbonate reservoirs is important for permeability estimates as well as reserve estimates having improved accuracy. Regarding clay-bound water, characterization of conventional clastic reservoirs can become complex in the presence of shale. The clay minerals in the shale contain tightly bound (i.e. claybound) water components with short $T_1$ and $T_2$ times. Deriving more accurate $T_1$ and $T_2$ times will improve the characterization of shaly-sand reservoirs by accurately quantifying the amount of clay-bound water and enabling the identification of different clay types by accurately determining the $T_1$ and $T_2$ positions of the clay types.

In support of the teachings herein, various analysis components may be used, including a digital and/or an analog system. For example, the NMR tool 10, the downhole electronics 11 or the computer processing system 12 may include digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure. Processed data such as a result of an implemented method may be transmitted as a signal via a processor output interface to a signal receiving device. The signal receiving device may be a computer display or a printer for presenting the result to a user. Alternatively or in addition, the signal receiving device may be a storage medium or memory for storing the result. Further, an alert maybe transmitted from the processor to a user interface if the result exceeds a threshold value. Further, the result may be transmitted to a controller or processor for executing an algorithm related to drilling or well completion that uses the result as input.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" and the like are intended to be inclusive such that there may be additional elements other than the elements listed. The conjunction "or" when used with a list of at least two terms is intended to mean any term or combination of terms. The term "configured" relates one or more structural limitations of a device that are required for the device to perform the function or operation for which the device is configured.

The flow diagram depicted herein is just an example. There may be many variations to this diagram or the steps (or operations) described therein without departing from the spirit of the invention. For instance, the steps may be performed in a differing order, or steps may be added, deleted or modified. All of these variations are considered a part of the claimed invention.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a property of a subsurface material, the method comprising:
   conveying a carrier through a borehole penetrating the subsurface material;
   performing an NMR measurement in a volume of interest in the subsurface material using an NMR tool disposed at the carrier, the NMR tool comprising an antenna;
   receiving with the antenna a short build-up signal due to a short magnetization build-up time of the NMR measurement;
   receiving with the antenna an echo-train signal with short polarization time due to the NMR measurement;
   receiving with the antenna an echo-train signal with long polarization time due to the NMR measurement,
   inverting, simultaneously, the short build-up signal, the short-polarization-time echo-train signal, and the long-polarization-time echo-train signal using a processor to estimate the property; and
   transmitting a signal comprising the property to a signal receiving device.

2. The method according to claim 1, wherein the subsurface material is characterized by at least one $T_2$ time of three milliseconds or less.

3. The method according to claim 2, wherein the subsurface material is characterized by at least one $T_2$ time of one hundred microseconds or more.

4. The method according to claim 1, wherein the short build-up signal, the short echo-train signal, and the long echo-train signal are obtained from one NMR measurement sequence.

5. The method according to claim 1, wherein the NMR measurement comprises a plurality of NMR measurements, each NMR measurement comprising an NMR measurement sequence, and one of the short build-up signal, the short-polarization-time echo-train signal, and the long-polarization-time echo-train signal is obtained from one NMR measurement sequence and the remaining signals are obtained from one or more other NMR measurement sequences.

6. The method according to claim 1, wherein inverting comprises establishing a linear combination of functions that best fits the short build-up signal, the short-polarization-time echo-train signal, and the long-polarization-time echo-train signal.

7. The method according to claim 6, further comprising establishing a norm approximation that minimizes error e between the linear combination of functions and the short build-up signal, the short-polarization-time echo-train signal, and the long-polarization-time echo-train signal.

8. The method according to claim 7, further comprising weighting data points in each of the short build-up signal, the short-polarization-time echo-train signal, and the long-polarization-time echo-train signal.

9. The method according to claim 8, wherein the weighting is in accordance with a signal-to-noise ratio (SNR) value associated with each of the data points such that data points associated with higher SNR values are weighted more than data points associated with lower SNR values.

10. The method according to claim 9, further comprising applying a penalty function to the norm approximation.

11. The method according to claim 10, wherein the penalty function comprises applying regularization to the norm approximation.

12. The method according to claim 10, further comprising establishing a generalized model representing the error e, the generalized model comprising a data weighting matrix W, a regularization matrix D representing a prior knowledge about a result a, a regularization parameter $\lambda$, and a parameter $r=T_1/T_2$.

13. The method according to claim 12, further comprising iterating r in the generalized model to determine a resulting r that provides a minimum sum of errors squared to provide a best fit curve.

14. The method according to claim 13, further comprising estimating the parameters using the best fit curve.

15. The method according to claim 1, wherein the property is total porosity or fractional porosity.

16. The method according to claim 1, further comprising displaying the property to a user using the signal receiving device.

17. The method according to claim 1, further comprising applying a wait (TW) time using the NMR tool for the NMR measurement comprising the long echo-train signal that is greater than the wait times for the NMR measurements of the short build-up signal and the short echo-train signal.

18. An apparatus for estimating a property of a subsurface material, the apparatus comprising:
- a carrier configured to be conveyed through a borehole penetrating the subsurface material;
- a nuclear magnetic resonance (NMR) tool disposed on the carrier and configured to perform an NMR measurement in a volume of interest in the subsurface material, the NMR tool comprising an antenna configured to at least one of transmit and receive electromagnetic energy; and
- a processor configured to:
    receive a short build-up signal received by the antenna due to a short magnetization build-up of the NMR measurement;
    receive a short echo-train signal using the antenna due to the NMR measurement;
    receive a long echo-train signal using the antenna due to the NMR measurement, the long echo-train comprising a greater number of echoes than the short echo-train, wherein a magnitude of magnetic polarization of atoms in the volume of interest emitting the long echo-train signal is greater than the magnitude of magnetic polarization of the atoms emitting the short build-up signal and the short echo-train signal;
    invert, simultaneously, the short build-up signal, the short echo-train signal, and the long echo-train signal using a processor to estimate the property; and
    transmit a signal comprising the property to a signal receiving device.

19. The apparatus according to claim 18, wherein the carrier comprises a wireline, a slickline, jointed drill pipe, or coiled tubing.

20. The apparatus according to claim 18, wherein the antenna comprises a plurality of antennas.

21. The apparatus according to claim 18, wherein the signal receiving device comprises a computer display or a printer configured to display the property to a user.

22. The apparatus according to claim 18, wherein the signal receiving device comprises memory or a storage medium.

23. The apparatus according to claim 18, wherein a wait time (TW) for the NMR measurement comprising the long echo-train signal is greater than the wait times for the NMR measurements comprising the short build-up signal and the short echo-train signal.

* * * * *